United States Patent [19]

Evans et al.

[11] Patent Number: 5,597,693
[45] Date of Patent: Jan. 28, 1997

[54] HORMONE RESPONSE ELEMENT COMPOSITIONS AND ASSAY

[75] Inventors: Ronald M. Evans; Kazuhiko Umesono, both of La Jolla, Calif.

[73] Assignee: The Salk Institute for Biological Studies, La Jolla, Calif.

[21] Appl. No.: 494,618

[22] Filed: Mar. 16, 1990

Related U.S. Application Data

[63] Continuation-in-part of Ser. No. 325,240, Mar. 17, 1989, abandoned.

[51] Int. Cl.$^6$ .............................. C12Q 1/68; C12P 21/02; C07K 7/06; C07K 14/705
[52] U.S. Cl. ........................... 435/6; 435/69.7; 530/330; 530/350
[58] Field of Search ....................... 435/6, 8, 15, 252.3, 435/69.7; 436/86, 87, 501; 935/60, 73; 530/300, 350, 330

[56] References Cited

U.S. PATENT DOCUMENTS

| | | | |
|---|---|---|---|
| 4,981,784 | 1/1991 | Evans et al. | 435/6 |
| 5,171,671 | 12/1992 | Evans et al. | 435/69.7 |
| 5,274,077 | 12/1993 | Evans et al. | 530/350 |

OTHER PUBLICATIONS

Green et al. Nature 325 (75–78) 1 Jan. 1987.
Green, et al., "The N–Terminal DNA–binding 'Zinc Finger' of the Oestrogen and Glucocorticoid Receptors Determines Target Gene Specificity", *EMBO J.* 7, No. 10, 3037–3044 (1988).
Klock, et al., "Oestrogen and Glucocorticoid Responsive Elements Are Closely Related But Distinct", *Nature* 329, 734–736 (1987).
Freedman, et al., "The Function and Structure of the Metal Coordination Sites Within the Glucocorticoid Receptor DNA Binding Domain", *Nature* 334, 543–546 (1988).
Severne, et al., "Metal Binding 'Finger' Structures in the Glucocorticoid Receptor Defined by Site–Directed Mutagenesis", *EMBO J.* 7, No. 8, 2503–2508 (1988).
Evans, R. M., "The Steroid and Thyroid Hormone Receptor Superfamily", *Science* 240, 889–895 (1988).
Mader, et al., "Three Amino Acids of the Oestrogen Receptor Are Essential to its Ability to Distinguish an Oestrogen From a Glucocorticoid Responsive Element", *Nature* 338, 271–274 (1989).

Thompson and Evans, "Trans–Activation by Thyroid Hormone Receptors: Functional Parallels With Steroid Hormone Receptors", *Proc. Natl. Acad. Sci. USA* 86, 3494–3498 (1989).
Umesono and Evans, "Determinants of Target Gene Specificity for Steroid/Thyroid Hormone Receptors", *Cell* 57, 1139–1146 (1989).
Hollenberg, S., and Evans, R., "Multiple and Cooperative Trans–Activation Domains of the Human Glucocorticoid Receptor", *Cell* vol. 55, 899–906 (Dec. 2, 1988).
Oro, A., Hollenberg, S., and Evans, R., "Transcriptional Inhibition by a Glucocorticoid Receptor–β–Galactosidase Fusion Protein", *Cell* vol. 55, 1109–1114 (Dec. 23, 1988).
Kumar, V., Green, S., Stack, G., Berry, M., Jin, J., and Chambon, P., "Functional Domains of the Human Estrogen Receptor", *Cell* vol. 51, 941–951 (Dec. 24, 1987).
Giguere, V., Hollenber, S., Rosenfeld, M., and Evans, R., "Functional Domains of the Human Glucocorticoid Receptor", *Cell* vol. 46, 645–652 (Aug. 29, 1986).
Giguere, V., Ong, E., Segui, P., and Evans, R., "Identification of a Receptor for the Morphogen Retinoic Acid", *Nature* vol. 330, 624–629 (Dec. 1987).
Kumar, V., and Chambon, P., "The Estrogen Receptor Binds Tightly to Its Responsive Element as a Ligand–Induced Homodimer", *Cell* vol. 55, 145–156 (Oct. 7, 1988).
Hollenberg, S., Giguere, V., Segui, P., and Evans, R., "Colocalization of DNA–Binding and Transcriptional Activation Functions in the Human Glucocorticoid Receptor", *Cell* vol. 49, 39–46 (Apr. 10, 1987).

*Primary Examiner*—Stephanie W. Zitomer
*Attorney, Agent, or Firm*—Pretty, Schroeder, Brueggemann & Clark; Stephen E. Reiter

[57] ABSTRACT

The present invention discloses steroid/thyroid hormone receptor DNA binding domain compositions that determine target gene specificity. The invention further discloses methods converting the target gene specificity of one receptor into the target gene specificity of another. Still further the invention discloses novel assays for identifying ligands for orphan hormone receptors. These assays are especially useful since they avoid the necessity of constructing chimeric genes and proteins in order to search for ligands that can activate a putative receptor.

10 Claims, 5 Drawing Sheets

FIG. 1A

```
              1    2            3    4                      5            6              7            8         9
hGR    421  CLVC SDEASGCHYGVLT CGSC KVFFKRAVEG--QHNYL CAGRNDC IIDKIRRKNCPA CRYRKC LQAGM 486
             ::::  :  : : ::   ::::   ::  :         :  : : ::     ::  :  :::     :::  :    :: ::
hTRβ   102  CVVC GDKATGYHYRCIT CEGC KGFFRRTIQKNLHPSYS CKYEGKC VIDKVTRNQCQE CRFKKC IYVGM 169        (44%)
             ::::  :    :  : :  ::::   :  :  :   :        :  : :    ::  :  :      ::  :    :: ::
hER    185  CAVC NDYASGYHYGVWS CEGC KAFFKRSIQG--HNDYM CPATNQC TIDKNRRKSCQA CRLRKC YEVGM 250        (55%)
```

```
GRE  :  AGAACAnnnTGTTCT
        ──→      ←──

ERE  :  AGGTCAnnnTGACCT
        ──→      ←──

TREp :  AGGTCA---TGACCT
        ──→   ←──
```

FIG. 2

|  | Finger 1 | | | | Linker | Finger 2 | | | | | MTV | TREp |
|---|---|---|---|---|---|---|---|---|---|---|---|---|
|  | 1 | 2 | 3 | 4 |  | 5 | 6 | 7 | 8 | 9 |  |  |
| hGRnx | CLVC | SDEASGCHYGVLT | CGSC | KVFFKRAVEG--QHNYL |  | CAGRNDC | IIDKIRRKNCPA | CRYRKC | LQAGM |  | 100 | — |
| GTG | .V.. | G.K.T.Y..RCI. | .EG. | .G..R.TIQKNLHPS.S |  | .KYEGK. | V...VT.NQ.QE | ..FK.. | IYV.. |  | — | 100 |
| GTG7 | .... | G.K.T.Y..RCI. | .... | ................. |  | ....... | ............ | ...... | ..... |  | 19 | — |
| GTG32 | .V.. | .............. | .EG. | .G..R.TIQKNLHPS.S |  | .KYEGK. | V...VT.NQ.QE | ..FK.. | IYV.. |  | — | 29 |
| GTG6 | .... | .............. | .... | ................. |  | ....... | ....VT.NQ.QE | ...... | ..... |  | 8 | — |
| GTG33 | .V.. | G.K.T.Y..RCI. | .EG. | .G..R.TIQKNLHPS.S |  | .KYEGK. | V........... | ..FK.. | IYV.. |  | — | 61 |
| GTG28 | .V.. | G.K.T.Y..RCI. | .EG. | .G..R.TIQKNLHPS.S |  | .KYEGK. | V........... | ...... | ..... |  | — | 74 |
| GTG26 | .V.. | .............. | .EG. | .G..R.TIQKNLHPS.S |  | .KYEGK. | V........... | ..FK.. | IYV.. |  | — | 62 |
| GTG21 | .V.. | .............. | .... | .G..R.TIQKNLHPS.S |  | .KYEGK. | V........... | ...... | ..... |  | — | 72 |
| GTG15 | .V.. | .............. | .... | .G..R.TIQKNLHPS.S |  | ....... | ............ | ...... | ..... |  | — | (2) |
| GTG5 | .... | .............. | .... | ................. |  | .KYEGK. | ............ | ...... | ..... |  | 17 | — |
| GTG8 | .... | .............. | .... | SIQKNM--V.T...... |  | ....... | ............ | ...... | ..... |  | 43 | — |
| GTG8A | .... | .............. | .EG. | .G..R.TIQK------- |  | ....... | ............ | ...... | ..... |  | — | — |
| GTG3B | .... | .............. | .... | TIQ-------------- |  | ....... | ............ | ...... | ..... |  | 88 | — |
| GTG3A | .... | .............. | .EG. | .G............... |  | ....... | ............ | ...... | ..... |  | — | — |
| GTG8B | .... | .............. | .EG. | .G............... |  | .KYEGK. | ............ | ...... | ..... |  | — | 97 |
| GTG36A | .V.. | G.K.T.Y..RCI. | .... | ....R.TIQKNLHPS.S |  | .KYEGK. | V...VT.NQ..Q | E.FK.. | IYV.. |  | — | 14 |
| GTG36B | .V.. | G.K.T.Y..RCI. | .EG. | .G..R....KNLHPS.S |  | .KYEGK. | V...VT.NQ..Q | E.FKK. | IYV.. |  | — | 7 |
| GTG29 | .V.. | G.K.T.Y..RCI. | .EG. | .G...RR.......... |  | .KYEGK. | V...VT.NQ..Q | E.FK.. | IYV.. |  | — | 7 |
| GTsstG | .V.. | G.K.T.Y..RCI. | .EG. | .G..R.TIQKSRHPS.S |  | .KYEGK. | V...VT.NQ..Q | E.FK.. | IYV.. |  | — | 21 |
| GRsst | .... | .............. | .... | .........S..R.... SELA |  | ....... | ............ | ...... | ..... |  | 58 | — |

|  | \|----- Finger 1 -----\| | \|---Linker---\| | \|------ Finger 2 ------\| | MTV | TREp | ERE |
|---|---|---|---|---|---|---|
|  | 1 2 3 | 4 | 5 6 7 8 9 |  |  |  |
| hGRnx | CLVC SDEASGCHYGVLT C | GSC KV FFKRAVEG--QHNYL | C AGRND C IIDKIRRKNCPA CRYRKC LQAGM | 100 | - | - |
| GTG | .V.. G.K.T.Y..RCI. | EG. .G ...R.TIQKNLHPS.S | . KYEGK . V...VT.NQ.QE ..FK.. IYV.. | - | 100 | 100 |
|  |  |  |  |  |  |  |
| GTG8B | ...................... | EG. .G .................. | ............ KYEGK ............................... | - | 97 | 330 |
| GTG21 | .V.................... | EG. .G ...R.TIQKNLHPS.S | . KYEGK . V........................................ | - | 72 | 300 |
|  |  | P | D |  |  |  |
| GTG3A | ...................... | EG. .G .................. | .................................................... | - | - | 250 |
| GTG15 | .V.................... | EG. .G ...R.TIQKNLHPS.S | .................................................... | - | (2) | 370 |
| GTG2 | ...................... | EG. .G .................. | .................................................... | 18 | - | 320 |
| GTG1 | ...................... | E. .................... | .................................................... | 110 | - | 40 |
|  |  |  |  |  |  |  |
| GTG5 | ...................... | ...................... | . KYEGK ............................................ | + | - | - |

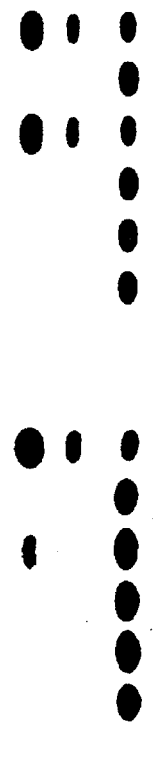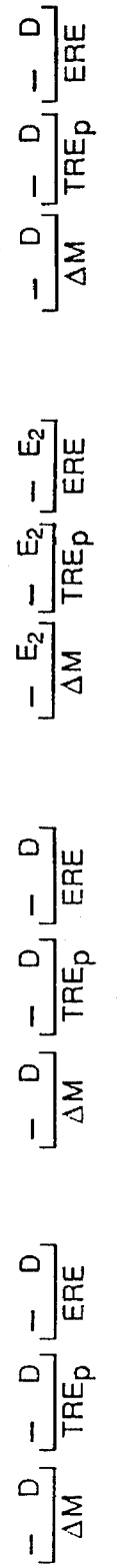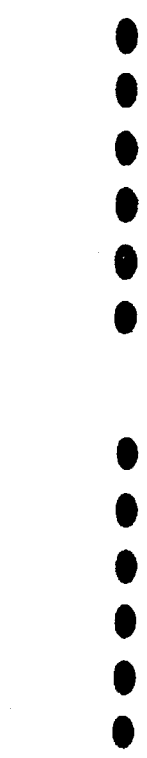

HORMONE RESPONSE ELEMENT COMPOSITIONS AND ASSAY

This invention was made with support from the Howard Hughes Medical Institute and grants from the National Institute of Health.

This application is a Continuation-In-Part of U.S. application Ser. No. 07/325,240 filed Mar. 17, 1989, now abandoned.

FIELD OF THE INVENTION

The present invention relates generally to hormone receptor genes and proteins. More particularly, the present invention relates to identification and characterization of determinants that govern target gene specificity for the superfamily of steroid/thyroid hormone receptors. In addition the invention relates to novel assays for identifying ligands for "orphan" hormone receptors.

BACKGROUND OF THE INVENTION

The steroid/thyroid hormone receptors form a superfamily of ligand-dependent transcription factors that influence cell function and fate in eukaryotes. It is known that these receptors transduce extracellular hormonal signals to target genes that contain specific enhancer sequences referred to as hormone-response elements (HREs) (Evans 1988; Green and Chambon 1988). It is also known that each receptor recognizes its own HREs, thus assuring that a distinct response is triggered by different hormones.

Sequence comparisons and mutational analyses of glucocorticoid receptor (GR) have identified functional domains responsible for transcriptional activation and repression, nuclear localization, DNA binding, and hormone binding (Gigure, et al., 1986; Hollenberg, et al., 1987; Rusconi, et al., 1987; Picard and Yamamoto, 1987; Hollenberg and Evans, 1988; Oro, et al., 1988a). The DNA binding domain, which is required to activate transcription, consists of 66–8 amino acids of which about 20 sites, including nine cysteines ($C_1$ to $C_9$), are invariant among different receptors (FIG. 1A). The modular structure of members of this receptor superfamily allows the exchange of one domain for another to create functional chimera. This strategy was used to demonstrate that the DNA binding domain is solely responsible for the specific recognition of the HRE in vivo (Green and Chambon, 1987; Giguere, et al., 1987; Petkovich, et al., 1987; Kumar, et al., 1987; Umesono, et al., 1988; Thompson, et al., 1989) and in vitro (Kumar and Chambon, 1988).

By analogy with the proposed structure for Xenopus transcription factor TFIIIA (Miller, et al., 1985), the invariant cysteines are thought to form two "zinc fingers" for specific DNA binding. In a polypeptide encompassing the DNA binding domain of rat GR, it has been shown that each of two Zn(II) is coordinated in a tetrahedral arrangement by four cysteines (Freedman, et al., 1988). Involvement of these cysteines in Zn(II) coordination is also supported by the fact that eight out of nine cysteines, enough to chelate two Zn(II), are required for the receptor function revealed by point mutagenesis experiments (Hollenberg, et al., 1988; Severne, et al., 1988).

Functional models have been proposed in an attempt to coordinate research results with gene regulation mechanisms that function in vivo. As those skilled in the art will know, one such model for the DNA binding domain is "zinc finger model". (A predicted "finger" structure is presented in FIG. 1B; also see Severne, et al., 1988.) In this model, the first four cysteines ($C_1$ to $C_4$) chelate one Zn(II) to form Finger 1, which includes a loop of 13 amino acids between $C_2$ and $C_3$. Finger 2 is formed by the next four cysteines ($C_5$ to $C_8$), since function is retained when the ninth cysteine is changed to an alanine or serine (Severne, et al., 1988). Finger 2 has a loop of 9 amino acids, and is separated by a "Linker" of 15–17 amino acids from Finger 1. Both fingers are functionally required because neither hGR Finger 1 or 2 by itself is sufficient to retain DNA binding and transactivation function (Hollenberg, et al., 1988). This finger model is applicable to all members of the receptor superfamily, indicating a common mode of HRE recognition by a receptor DNA binding domain.

The HREs are structurally related but in fact are functionally distinct. Those for GR (GRE), estrogen receptor (ER) (ERE), and the thyroid receptors ($T_3Rs$) (TRE) have been characterized in detail; they consist of a palindromic pair of "half sites" (FIG. 1C) (Evans, 1988; Green and Chambon, 1988). With optimized pseudo- or consensus response elements, only two nucleotides per half site are different in GRE and ERE (Klock, et al., 1987). On the other hand, identical half sites can be seen in ERE and TRE, but their spacing is different (Glass, et al., 1988). Thus, at least two different means are used to achieve HRE diversity.

As the present invention discloses, functional characterization of mutant receptors carrying chimeric DNA binding domains has made it possible to dissect molecular determinants of target gene specificity for GR, ER, and TR. For example, as the present invention discloses, the identity of GR DNA binding domain can be converted into those of ER and TR by changing three and eight amino acids, respectively. The present invention also discloses that a single Gly to Glu change in the first "zinc finger" of the GR receptor produces a receptor with dual HRE (i.e., GRE and ERE) sequence responsiveness. These discoveries localize two structural determinants of target gene specificity and suggest a simple pathway for the co-evolution of receptor DNA binding domains and regulatory networks.

These discoveries also make it possible to convert one receptor into another, and to create engineered receptors that have desired HRE recognition features. They have also enabled the development of assays that are useful for identifying ligands for "orphan" hormone receptors. Such assays are especially advantageous because they eliminate the necessity of constructing chimeric genes and proteins in order to search for ligands that can activate the orphan receptors.

BRIEF DESCRIPTION OF THE DRAWINGS

The following is a brief description of the drawings. More detailed descriptions are found in the section of the specification labeled, "Detailed Description of the Drawings".

FIGS. 1A–1C are schematic drawings. FIG. 1A shows a comparison of amino acid sequences among the DNA binding domains of hGR, $hT_3\beta$, and hER. FIG. 1B shows predicted zinc fingers based on those for rat GR18. FIG. 1C shows the structures of optimized hormone response elements for GR (GRE), ER (ERE), and $T_3R$ (TRE).

FIG. 2 is a schematic drawing that illustrates transactivation of luciferase reporter plasmids by mutant receptors.

FIG. 3 is a schematic drawing that illustrates identification of two distinct elements specifying the TREp+ and ERE+ phenotypes.

FIGS. 4A–4H is comprised of the combination of schematic drawings and photographs of blots. FIGS. 4A–4H show induction of CAT activities by mutant receptors from the basal ΔMTV-CAT (ΔM), T$_3$-responsive ΔMTV-TREp-CAT (TREp), and estrogen-responsive AMTV-ERE-CAT (ERE) reporters The specific receptors shown are 4A: no receptor; 4B: hGRnx; 4C: hER; 4D: GTG; 4E: GTG8B; 4F: GTG3A; 4G: GTG2; and 4H: GTG1.

DEFINITIONS

Figures 1B, 1C:
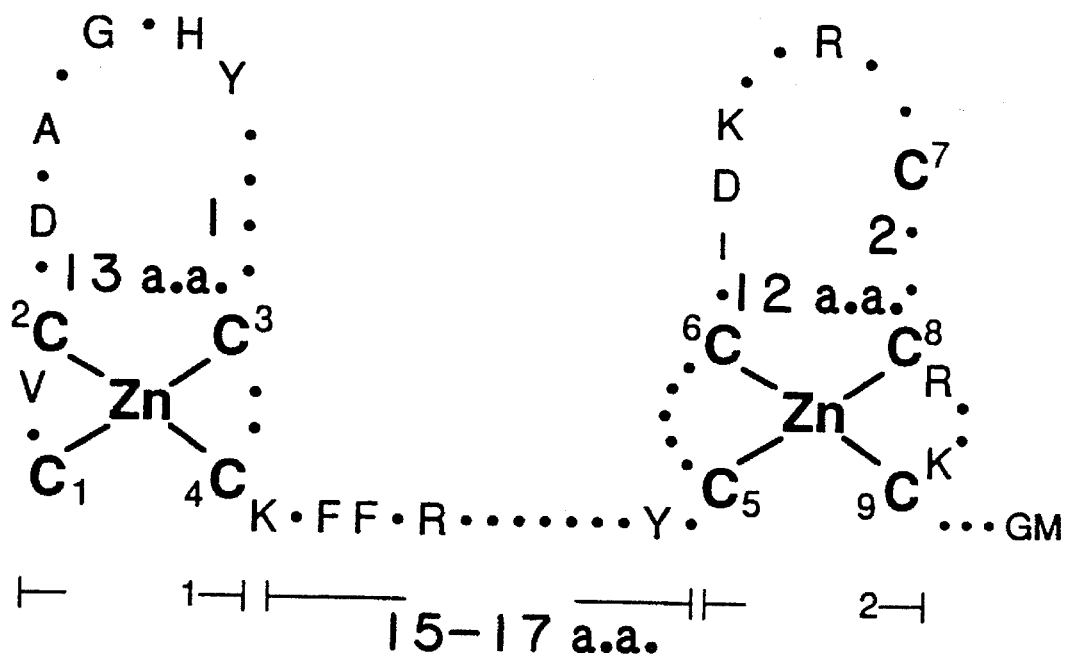

In the present specification and claims, reference will be made to phrases and terms of art which are expressly defined for use herein as follows:

As used herein, species are identified as follows: h, human; r, rat; m, mouse; c, chicken; and d, Drosophilia.

As used herein, "steroid hormone superfamily of receptors" refers to the class of related receptors comprised of glucocorticoid, mineralocorticoid, progesterone, estrogen, estrogen-related, vitamin D$_3$, thyroid, v-erb-A, retinoic acid and E75 (Drosophilia) receptors. See Evans (1988) and the references cited therein.

As used herein, GR means glucocorticoid receptor. The DNA referred to as hGR codes for human glucocorticoid receptor GR. hGR is encoded by plasmid pRShGR which has been deposited for patent purposes and accorded ATCC No. 67200.

As used herein, MR means mineralocorticoid receptor. The DNA referred to as hMR codes for human mineralocorticoid receptor MR. hMR is encoded by plasmid pRShMR which has been deposited for patent purposes and accorded ATCC No. 67201.

As used herein, TR means thyroid receptor and T$_3$R means triiodothyronine (T$_3$) receptor. TRα and TRβ refer to the alpha and beta forms of the thyroid receptor. Plasmid pherb-A 8.7 encodes hTRα; it has been deposited for patent purposes and accorded ATCC No. 40374. Plasmid peA101 encodes hTRβ; it has been deposited for patent purposes and accorded ATCC No. 67244.

As used herein, ERR means estrogen-related receptor. The acronyms, hERR1 and hERR2 refer to human estrogen-related receptors 1 and 2. These receptors are more related to steroid receptors than to the thyroid receptors, yet they go not bind any of the major classes of known steroid hormones (Giguere, et al., 1988). hERR1 is encoded by plasmids pE4 and pHKA, which have been deposited for patent purposes and accorded ATCC No. 67309 and 67310, respectively. (Neither pE4 or pHKA are complete clones; hERR1 is constructed by joining segments from both clones.) hERR2 is encoded by plasmid phH3 which has been deposited for patent purposes and accorded ATCC No. 40373.

As used herein, RAR means retinoic acid receptor. The acronym, hRARα, refers to human retinoic acid receptor alpha. hRARα is encoded by plasmid phRARα which has been deposited for patent purposes and accorded ATCC No. 40392.

As used herein, VDR means vitamin D$_3$ receptor.

As used herein, an "orphan" receptor is a protein encoded by a DNA sequence that is homologous with DNA sequences that encode known members of the steroid/thyroid superfamily of hormone receptors. The term "orphan" denotes the fact that the ligand(s) which bind to the putative receptor are not yet known.

As used herein, element P means one of two clusters of amino acids in the steroid/thyroid receptors that can differentially control target gene specificity of the DNA binding domains. The cluster of amino acids that comprise element P for the GR subfamily (GR, MR, PR, AR) is "GSCKV"; the clusters that comprise element P for the ER subfamily (T$_3$Rα, T$_3$α, RARα, RARβ, VD$_3$R, NGFI-B, TR$_2$, v-erbA, ear2, ear3, Knirps, Knirps-related, ERR1, ERR2) are "EGCKA", "EGCKG", "EGCKS", and "EACKA". Also see Table 2.

As used herein, element D means one of two clusters of amino acids in the steroid/thyroid receptors that can differentially control target gene specificity of the DNA binding domains. The clusters of amino acids that comprise element D for the GR subfamily (GR, MR, PR, AR) are "AGRND" and "ASRND"; the clusters that comprise element D for the ER subfamily (T$_3$Rα, T$_3$α, RARα, RARβ, VD$_3$R, NGFI-B, TR$_2$, v-erbA, ear2, ear3, Knirps, Knirps-related, ERR1, ERR2) are "PATNQ", "KYDSC", "KYEGK", "HRDKN", "PFNGD", "LANKD", "RGSKD", "TYDGC", "RSNRD", "RANRN", "KNEGK", "KNNGE", "PASNE", and "PATNE". Also see Table 2.

As used herein, CAT means chloramphenicol acetyltransferase.

As used herein, luciferase means firefly luciferase. See, de Wet, et al., (1987).

As used herein, COS means monkey kidney cells which express T antigen (Tag). See Gluzman, Cell, 23:175 (1981).

As used herein, CV-1 means mouse kidney cells from the cell line referred to as "CV-1". CV-1 is the parental line of COS. Unlike COS cells, which have been transformed to express SV40 T antigen (Tag), CV-1 cells do not express T antigen. CV-1 cells are receptor-deficient cells that are also useful in the assays of the present invention.

As used herein, HRE means hormone response element. HREs are short cis-acting sequences (about 20 bp in size) that are required for hormonal (or ligand) activation of transcription. The attachment of these elements to an otherwise hormone-nonresponsive gene causes that gene to become hormone responsive. HREs function in a position- and orientation-independent fashion. Unlike other enhancers, the activity of the HREs is dependent upon the presence or absence of ligand. See Evans (1988) and the references cited therein.

As used herein, engineered HREs refer to HREs that have been recombinantly produced using genetic engineering techniques such as nucleotide substitution, deletion, etc. If wild-type, engineered or synthetic HREs are linked to hormone-nonresponsive promoters, these promoters become hormone responsive. See Evans (1988) and the references cited therein.

As used herein, synthetic HREs refer to HREs that have been synthesized in vitro using automated nucleotide synthesis machines. Since the HREs are only about 20 bp in size, they are easily synthesized in this manner. If wild-type, engineered or synthetic HREs are linked to hormonenonresponsive promoters, these promoters become hormone responsive. See Evans (1988) and the references cited therein.

As used herein, the acronym GRE means glucocorticoid response element and TRE means thyroid receptor response element. GREs are hormone response elements that confer glucocorticoid responsiveness via interaction with the GR. See Payvar, et al., Cell, 35:381 (1983) and Schiedereit, et al., Nature, 304:749 (1983). GREs can be used with any wild-type or chimeric receptor whose DNA-binding domain can functionally bind (i.e., activate) with the GRE. For example, since GR, MR and PR receptors can all activate GREs, a GRE can be used with any wild-type or chimeric receptor that has a GR, MR or PR-type DNA-binding domain. TREs are similar to GREs except that they confer thyroid hormone responsiveness via interaction with TR. TREs can be used with any wild-type or chimeric receptor whose DNA-binding domain can functionally bind (i.e., activate) with the TRE. Both TR and RR receptors can activate TREs, so a TRE can be used with any receptor that has a TR or RR-type DNA-binding domain.

As used herein, ligand means an inducer, such as a hormone or growth substance. Inside a cell the ligand binds to a receptor protein, thereby creating a ligand/receptor complex, which in turn can bind to an appropriate hormone response element. Single ligands may have multiple receptors. For example, both the $T_3R\alpha$ and the $T_3R\beta$ bind thyroid hormone such as $T_3$.

As used herein, the word "operative", in the phrase "operative hormone response element functionally linked to a ligand-responsive promoter and an operative reporter gene", means that the respective DNA sequences (represented by the terms "hormone response element", "ligand-responsive promoter" and "reporter gene") are operational, i.e., the hormone response element can bind with the DNA-binding domain of receptor protein (either wild-type or chimeric), the ligand-responsive promoter can control transcription of the reporter gene (upon appropriate activation by a HRE/receptor protein/ligand complex) and the reporter gene is capable of being expressed in the host cell. The phrase "functionally linked" means that when the DNA segments are joined, upon appropriate activation, the reporter gene (e.g., CAT or luciferase) will be expressed. This expression occurs as the result of the fact that the "ligand responsive promoter" (which is downstream from the hormone response element, and "activated" when the HRE binds to an appropriate ligand/receptor protein complex, and which, in turn then "controls" transcription of the reporter gene) was "turned on" or otherwise activated as a result of the binding of a ligand/receptor protein complex to the hormone response element.

As used herein, the phrase "DNA-binding domain" of receptors refers to those portions of the receptor proteins (such as glucocorticoid receptor, thyroid receptor, mineralocorticoid receptor, estrogen-related receptor and retinoic acid receptor) that bind to HRE sites on the chromatin DNA. The boundaries for these DNA-binding domains have been identified and characterized for the steroid hormone superfamily. See Evans, (1988); also see Giguere, et al., (1986); Hollenberg, et al., (1987); Green and Chambon (1987); Miesfield, et al., (1987); and Evans (1988).

The DNA-binding domains of the steroid hormone superfamily of receptors consist of an amino acid segment varying between 66 to 68 amino acids in length. This segment contains 9 cysteine residues, one of which is the first amino acid of the segment. This first Cys residue begins a motif described as $CyS-X_2-CyS-X_{13-15}-CyS-X_2-Cys$, where X is any amino acid residue. The DNA-binding domain invariably ends with the amino acids Gly-Met.

As used herein, the phrase "ligand-binding domain region" of receptors refers to those portions of the receptor proteins that bind to ligands such as growth substances or the hormones. These boundaries of the ligand-binding domains for the steroid receptor superfamily have been identified and characterized. See Evans (1988).

As used herein, "mutating" means using genetic engineering techniques to alter DNA so that it is different from the "wild-type" or unmodified sequences. Useful genetic engineering techniques for altering the DNA include, but are not limited to, insertion of new nucleotides into wild-type sequences, deletion of nucleotides from wild-type sequences, and substitution of nucleotides in the wild-type sequences, for example by site directed mutagenesis.

As used herein, "mutant" DNA of the invention refers to DNA that has been genetically engineered to be different from the "wild-type" or unmodified sequences. Such genetic engineering includes insertion of new nucleotides into wild-type sequences, deletion of nucleotides from wild-type sequences, or substitution of nucleotides in the wild-type sequences, for example by site directed mutagenesis.

Use of the term "substantial sequence homology" in the present specification and claims means it is intended that DNA, RNA, or amino acid sequences which have slight and non-consequential sequence variations from the actual sequences disclosed and claimed herein are within the scope of the appended claims. In this regard, the "slight and non-consequential" sequence variations mean that the homologous sequences will be functionally equivalent to the sequences of the invention, i.e., the homologous sequences function in substantially the same manner to produce substantially the same compositions as the nucleic acid and amino acid compositions disclosed and claimed herein.

As used herein, the term "recombinantly produced" means made using genetic engineering techniques, not merely purified from nature.

The amino acids which comprise the various amino acid sequences appearing herein may be identified according to the following three-letter or one-letter abbreviations:

| Amino Acid | Three-Letter Abbreviation | One Letter Abbreviation |
| --- | --- | --- |
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

The nucleotides which comprise the various nucleotide sequences appearing herein have their usual single-letter designations (A, G, T, C or U) used routinely in the art.

As used herein, bp means base pairs and kb means kilobase pairs.

In the present specification and claims, the Greek letters alpha ($\alpha$), beta ($\beta$), gamma ($\gamma$), etc., are sometimes referred to as a, b, g, etc.

In the present specification and claims, unless noted otherwise, temperatures are in degrees Centigrade.

DEPOSITS

Plasmids pRShGR (hGR), pRShMR (hMR), peA101 (Ht$_3\beta$) and GMCAT, all of which are in *E. coli* HB101, plus plasmids pE4 and pHKA (which together encode hERR1), phH3 (hERR2), pherb-A 8.7 (hTRα, phFA 8 (a partial clone of hTRα, and plasmid phRARα have been deposited at the American Type Culture Collection, Rockville, Md., U.S.A. (ATCC) under the terms of the Budapest Treaty on the International Recognition of Deposits of Microorganisms for Purposes of Patent Procedure and the Regulations promulgated under this Treaty. Samples of the plasmids are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

The ATCC Deposit Numbers and Deposit Dates for the deposits are as follows:

| pRShGR (hGR) | 67200 | Sept. 9, 1986 |
| pRShMR (hMR) | 67201 | Sept. 9, 1986 |
| pE4 (hERR1*) | 67309 | Jan. 30, 1987 |
| phHKA (hERR1*) | 67310 | Jan. 30, 1987 |
| phH3 (hERR2) | 40373 | Sept. 29, 1987 |
| GMCAT (reporter) | 67282 | Dec. 18, 1986 |
| pherb-A 8.7 (hTRα) | 40374 | Sept. 29, 1987 |
| peA101 (hTRβ) | 67244 | Oct. 22, 1986 |
| phRARα (hRARα) | 40392 | Nov. 20, 1987 |

(*means a partical clone)
(pE4 & phHKA together encode complete hERR1)

SUMMARY OF THE INVENTION

The present invention discloses steroid/thyroid hormone receptor DNA binding domain compositions that determine target gene specificity. The invention further discloses methods for converting the target gene specificity of one receptor into the target gene specificity of another. Still further the invention discloses novel assays for identifying ligands for orphan hormone receptors. These assays are especially useful since they avoid the necessity of constructing chimeric genes and proteins in order to search for ligands that can activate a putative receptor.

DESCRIPTION OF THE INVENTION

In one aspect, the present invention comprises steroid/thyroid hormone receptor DNA binding domain compositions that determine target gene specificity. The compositions of the invention are selected from the group consisting of GSCKV, EGCKA, EGCKG, EGCKS, EACKA, AGRND, ASRND, PATNQ, KYDSC, KYEGK, HRDKN, PFNGD, LANKD, RGSKD, TYDGC, RSNRD, RANRN, KNEGK, KNNGE, PASNE, and PATNE.

In another aspect, the present invention is a cluster of amino acids comprised of EGxxGxxR where x is selected from the group consisting of A, R, N, D, C, Q, E, H, I, L, K, M, F, P, S, T, W, Y, and V.

In still another aspect, the present invention is a cluster of amino acids comprised of KVEGK.

In still another aspect, the present invention is comprised of mutant receptors selected from the group consisting of GTG8B, GTG3A, GTG2, GTG1.

In still another aspect, the invention comprises a method for constructing a receptor that can activate both GRE and ERE sequences. The method comprises introducing a point mutation into the glucocorticoid receptor DNA sequence so that the encoded glycine at the site between $C_3$ and $C_4$ is replaced with a glutamic acid. Conversely, a point mutation is introduced into the estrogen receptor DNA sequence so the encoded glutamic acid at the site between $C_3$ and $C_4$ is replaced with a glycine.

In still another aspect, the invention comprises a substantially pure receptor protein that can activate both glucocorticoid and estrogen response element sequences.

In still another aspect, the invention comprises methods for converting the target gene specificity of one receptor into the target gene specificity of another. According to this aspect of the invention, target gene specificity of the glucocorticoid receptor is converted to that of the estrogen receptor by changing three amino acids clustered in the first zinc finger. A single Gly to Glu change in this region produces a receptor with dual sequence responsiveness. Further replacement of five amino acids in the stem of the second zinc finger transforms the specificity to that of the thyroid hormone.

Still further the invention comprises novel assays for identifying functional ligands for orphan hormone receptors. These assays are especially useful since they avoid the necessity of constructing chimeric genes and proteins in order to search for ligands that can activate an orphan receptor. In addition, the assays of the invention do not require that the DNA sequences in question be sequenced to see if they belong to the GR or ER/TR subfamilies (although this can be done). Furthermore, as is done in the preferred assay of the invention, the presence of two reporter genes in the host cell, one operatively linked to a GRE and the other to a ERE, makes it possible to assay all unknown members of the steroid/thyroid receptor superfamily with a single assay system. In addition, a cocktail of ligands can be tested at once. If any of the ligands activate either of the reporters these ligands can be retested, e.g., in smaller "cocktail" groups, and then separately. This greatly increases the efficiency of the search for ligands for the orphan receptors.

According to one assay aspect of the invention, DNA sequences are isolated that are suspected of encoding receptor proteins. These DNA sequences are transfected into a suitable receptor-deficient host cell that has been engineered to contain at least one reporter gene functionally linked to at least one operative hormone responsive element wherein the hormone response element(s) is selected from the group consisting of wild-type, engineered or synthetic glucocorticoid response element and wild-type, engineered or synthetic estrogen response element. The transfected receptor-deficient host cell (which now contains the suspected or "orphan" receptor and at least one reporter/HRE complex) is challenged with at least one candidate ligand(s) that can potentially bind with the ligand-binding domain region of the putative receptor protein encoded by the DNA sequence in question. The induction of the reporter gene is monitored by means of changes in the protein levels of the protein encoded by the reporter gene. Finally a selection is made of ligand(s) that is capable of inducing production of the protein product of the reporter gene.

In preferred assays of the invention, the transfected host cell be a CV-1 cell which will contain at least two reporter genes, each operatively linked to a different functional HRE element. In an especially preferred form, a first reporter gene will be operatively linked to wild-type, engineered or synthetic glucocorticoid response element, and a second will be operatively linked to wild-type, engineered or synthetic estrogen response element. In this form, a first reporter gene will preferably be chloramphenicol acetyltransferase (CAT) and the second will preferably be firefly luciferase.

In another assay aspect of the invention, an assay is provided for identifying ligand(s) that activates an orphan receptor. According to this aspect of the invention, receptor-deficient host cells are provided with at least one reporter gene functionally linked to a preselected hormone response element. In addition, at least the DNA encoding the P region of the DNA binding domain of the orphan receptor is mutated, preferably by means of site directed mutagenesis, so that the mutated orphan receptor can activate the preselected hormone response element in receptor-deficient host cells. The host cells containing the preselected hormone response element functionally linked to at least one reporter gene are contacted with mutated orphan receptor, and then challenged with candidate ligand(s) which can potentially bind with the ligand-binding domain region of the mutated orphan receptor. Finally, induction of the reporter gene(s) is monitored as an indication of those ligand(s) which can activate the orphan receptor.

The compositions, methods and assays of the invention, plus preferred methods for making and using them, are described more fully in the Examples that follow.

EXAMPLES

EXAMPLE 1

Finger Module

Previous studies on hormone receptors have shown that amino acids throughout the entire DNA-binding domain may be important for DNA-binding (Hollenberg, et al., 1987). This example discloses which amino acids contribute to sequence recognition and are thus responsible for determining target gene specificity. Experimentally, it is important to know what changes in the DNA binding domain are necessary, at a minimum, to allow the glucocorticoid receptor to recognize thyroid hormone and estrogen response elements. Between the human glucocorticoid receptor (hGR) and the human thyroid receptor beta (hTRβ) less than half of the amino acids in this region are conserved (FIG. 1A). If the entire hGR DNA binding domain is replaced by that from the hTRβ, specificity is completely switched such that hybrid GTG activates only through the TRE and no longer recognizes the GRE (Thompson, et al., 1989).

In the present experiment mutant GR expression plasmids were introduced into monkey kidney CV-1 cells together with at least one reporter plasmid (e.g., one of the firefly luciferase reporter plasmids) to test its target gene specificity and transactivation function. For glucocorticoid response the luciferase coding sequence was linked to the responsive MTV-LTR (MTV-LUC plasmid) (Hollenberg, et al., 1988). For $T_3$-responsiveness the GREs were deleted from MTV and replaced with an oligonucleotide encoding a palindromic TRE to generate reporter ΔMTV-$TRE_p$-LUC (Umesono, et al., 1988; Giguere, et al., 1989). Upon addition of a synthetic glucocorticoid dexamethasone, parental receptors hGRnx and GTG elicited around 2,500 and 200 fold induction over the background level from MTV-LUC and ΔMTV-$TRE_p$-LUC, respectively (FIG. 2). These inductions are clearly mediated by the cognate response elements.

EXAMPLE 2

Receptor Identity: TRE Recognition

To identify amino acids that allow the receptors to discriminate between their cognate HREs, a variety of chimeric DNA binding domains were constructed. In the mutants presented in FIG. 2, portions of the loops and linkers were exchanged between the hGR and hTRβ or human retinoic acid receptor alpha (hRARα). These switches of Loop 1 (GTG7 and GTG32), most parts of the Linker (GTG3A, GRG8, GTG36B, and GTG29), and Loop 2 and adjacent downstream portions (GTG6, GTG33, and GTG28). All of these switch mutants are active (88% to 7% of parental response) upon induction of a luciferase activity.

The interchangeable nature of the loops is remarkable in terms of dramatic changes in charge distribution with no change in target gene specificity. Furthermore, both small and large substitutions in the Linker regions are quite forgiving with no impact on promoter specificity. Reducing or expanding the spacing between the fingers from 15 (GRnx and GTG29), 17 (GTG), 19 (GRsst) and 21 (GRsstG) is again well tolerated. From phenotypes of these mutants, it is apparent that differences in the primary structure or size found in these regions are mutually permissive even between two of the most distantly related members of the receptor superfamily. Furthermore, since none of the Loop or Linker mutants described here has changed specificity, it is concluded that these amino acids apparently are not critical in discriminating between GREs and TREs or $TRE_p$ from GREs, but rather are involved in common aspects of HRE recognition and transactivation.

The modular or interchangeable nature of large segments of the finger regions does not belie the fundamental fact that there must be sequences that determine specificity. By elimination from this series of mutants, nine amino acids in two clusters were not changed and may therefore impart specificity. The first proximal (P) region follows $C_3$ and includes the three amino acid cluster GS-V in the GR and EG--G in the TR. These are part of a 10 amino acid segment that is highly conserved and includes 6 invariant amino acids. When these three amino acids are switched (see GTG3A in FIG. 2 and GTG36A in FIG. 2), the resultant chimeras are nonfunctional on either MTV-LUC or ΔMTV-$PRE_p$-LUC. The second or distal (D) region of potential importance in specificity is a cluster of five amino acids between $C_5$ and $C_6$; AGRND in hGR and KYEGK in hTRβ.

Indeed, elimination of these amino acids from GTG21 to produce GTG15 yields a TRE inactive phenotype (FIG. 3). Based on these observations the critical double switch and mutant GTG8B (FIG. 3) was constructed which carries an almost complete hGR DNA-binding domain with only 8 hTRβ-specific amino acids. Remarkably, this chimera induces a full conversion of target gene specificity (FIGS. 3 and 4E). The induction of luciferase activity on the $TRE_p$ reporter by GTG8B is as efficient as GTG itself.

Thus two noncontiguous "elements" (P and D) have been localized in the hTRβ DNA-binding domain that are sufficient to impart TRE-specific recognition in the context of an otherwise normal glucocorticoid receptor. Both elements are necessary while neither alone is sufficient. Furthermore, acquisition of the TRE specificity in this change includes a complete loss of GRE responsiveness.

EXAMPLE 3

Receptor Identity: ERE Recognition

Although all HREs contain a recognizable conserved motif, the TREp and the palindromic vitellogenin ERE (EREp) differ only in the spacing of what are otherwise identical half-sites (5'-TGACC-3', FIG. 1C). Furthermore, recent studies indicate that the endogenous $T_3R$ (Glass, et al., 1988) as well as the in vitro translated product of cloned α and β TR cDNA (Thompson et al., 1989) can bind with high affinity to both EREp as well as TREp. Despite this relationship, the possibility that the $T_3R$ might mediate an ERE-dependent transactivation has not been carefully evaluated. To address this issue an oligonucleotide encoding the ERE was inserted into the basal ΔMTV promoter (Hollenberg, et al., (1988)) to make reporter plasmids ΔMTV-ERE-LUC and ΔMTV-ERE-CAT.

This promoter is indeed estradiol ($E_2$) infusible because in CV-1 cells an efficient stimulation of CAT activity is dependent on both functional ER and the ligand $E_2$ (FIG. 4D). The transfected HER fails to activate through the GRE (Umesono and Evans, unpublished data) but does sustain a weak activator of the TREp reporter. However, in the reciprocal experiment the GTG chimera promotes activity of the ERE reporter (FIGS. 3 and 4D). In contrast, hGR does not induce CAT or luciferase activity from a EREp or TREp receptor (FIGS. 3 and 4B). Thus, the DNA binding domain of $hT_3R\beta$ is able to recognize both the TREp and ERE as response elements in this assay system.

Because of this close relationship between the HER and hTR mutant receptors were tested for combined ERE and TRE responsiveness to evaluate functional roles for the two specificity regions. Taking the activity of GTG as 100%, all of the TRE+ mutants in FIGS. 2 and 3 (GTsstG, GTG32, GTG36B, GTG29, GTG28, GTG21, and GRGS) showed 70% to 650% activity upon the ERE reporter (FIG. 3). Furthermore, mutants carrying hTRβ element P but lacking element D (GTG15 and GTG3A) also showed significant inductions upon ERE even though they were inactive on the $TRE_p$ (FIGS. 3 and 4F). These results demonstrate that $hT_3R\beta$ element P, not D, determines a positive phenotype upon the common TGACC-type half sites found in ERE and $TRE_p$. Consistently all the mutants containing GR element P (hGRNX, GTG7, GRG8, GTG6, GTG36A, GTG5) are not responsive to the ERE reporter (data not shown).

The phenotype of GTG3A (FIGS. 3 and 4F) has clearly revealed that replacement of three amino acids, forming element P, is sufficient to convert the identity of hGR DNA binding domain (GRE$^+$, ERE$^-$, TRE$^-$) into that of ER (GRE$^-$, ERE$^+$, TRE$^-$). It is noteworthy that this is a complete conversion; that is, this mutant is negative upon MTV and only positive upon ERE. The ERE responsiveness of mutant GTG3A is not restricted to the modified MTV promoter. For example, ERE-TK-LUC reporter is also regulated by GTG3A while the parental TK-LUC that lacks an oligonucleotide encoding ERE is not induced (unpublished observations).

EXAMPLE 4

Receptor Identity: Dual Specificity

The data presented herein have shown that element P, located in the base of Finger 1 and part of the adjacent Linker specifies the GRE-ERE responsiveness. This element includes three amino acid differences between hGR (GSCKV) and $hT_3R\beta$. Interestingly $hT_3R\beta$ and hER (EGCKA), both of which are active upon ERE, share almost identical structures when it comes to this element (FIG. 1A), indicating that these amino acid sequences are important for the recognition of ERE.

One trend of these results is that by imparting a new specificity upon a DNA-binding domain, the previous binding specificity is simultaneously lost. To determine whether individual amino acids play different roles with regard to acquisition or suppression of HRE specificity, the activity of single paired and triple mutants was examined. Although the triple mutant (GTG3A) selectively recognizes the ERE, the double mutant (GTG2) is active upon both MTV and ERE reporters (FIG. 3 and 4F). This induction is dependent on the HRE since this receptor fails to activate either ΔMTV or TREp promoter (FIG. 4F). An examination of the phenotype of this mutant indicates that the last glycine in the $T_3R\beta$ P element seems to be involved in a suppression of the GRE$^+$ without a substantial impact on ERE recognition.

Based on this result the question was asked whether a single amino acid substitution would be sufficient to impart a recognizable change on receptor phenotype. Remarkably, by substituting the glucocorticoid receptor glycine or an estrogen receptor glutamic acid between $C_3$ and $C_4$ (GTG1) a receptor with dual specificity is produced. This single amino acid change leaves GRE recognition normal but fosters clear recognition of the ERE. As with GTG2 mutant, these inductions are dependent on either GREs or EREs (FIG. 3 and 4H). However, because all of these mutants lack the $T_3R\beta$ D element, they are completely inactive on the TREp.

EXAMPLE 5

The P and D Elements

As those skilled in the art will appreciate, the results presented in the previous Examples provide a number of unexpected conclusions concerning the mechanisms by which the nuclear receptors identify their appropriate response elements. First, the putative loops of the two zinc fingers can be exchanged between receptors without altering specificity. Second, two distinct regions, P and D, outside the loops, are critical for sequence recognition. Third, different amino acids may be involved in acquisition and loss of HRE responsiveness. Because of this, it has been possible via a single amino acid change to create a receptor with dual GRE and ERE recognition.

It is important to understand that these results do not imply that the amino acids in the loops are not critical for sequence specific binding; rather our results show that the amino acids in the loops are not critical in identifying the differences between response elements. Thus, it may be presumed that the commonalty of loop function indicates that they mediate recognition of common aspects of HRE structure. In contrast, the P and D elements would be involved in recognizing the variant nucleotides. This is consistent with the observation that HREs are composed of a common core sequence that can change in only a restricted number of nucleotide positions. This would suggest a putative topographical alignment between the HRE and the zinc finger such that the variable region of the HRE would always align with the P element of the finger. It can therefore be presumed that amino acids in this element make specific contacts with at least one of the variable positions in the pentomeric HRE.

In addition to primary sequence recognition there is a need to discriminate half-site spacing (ERE vs. TRE; FIG. 1C). As summarized in Table 1, our results indicate that the first element (P) specifies the primary nucleotide sequence of the half sites, while the second element (D) is important for the determination of the half-site spacing. In other words the second element in the hGR and hER restricts recognition to HREs with three gap nucleotides.

In respect to the amino acid sequence of the first element, all members of this receptor superfamily can be classified into either GR or ER subfamily (Table 2). The GR subfamily includes four members (GR, MR, PR, and AR (Evans, 1988); Lubahn, et al., 1988); Ham, et al., 1988), and all of them are able to recognize GREs, although physiological effects of each hormone are quite different (Ham, et al., 1988). The other members constitute the ER/TR subfamily (ER, $T_3R\alpha$, $T_3R\beta$, RAR$\alpha$, RAR$\beta$, $VD_3R$, NGFI-B (Milbrandt, 1988), TR-2 (Chang, et al., 1988), v-erbA, ear2 (Miyajima, et al., 1988), ear3 (Miyajima, et al., 1988), knirps (Nauber, et al., 1988), knirps-related (Oro, et al., 1988b), ERR1 and ERR2 (for reference, see Evans, 1988) with a slight variation. The members of this subfamily may recognize ERE, TREp, or a palindromic pair of TGACC sequences separated by five or more gap nucleotides because of the critical glutamic acid residue following $C_3$. In support of this model, our group at the Salk Institute for Biological Studies has shown that retinoic acid receptor can bind to and activate transcription through TREp.

Compared to the structural conservation of the first element, the second element is quite divergent. According to our hypothesis the second element need not bind directly to DNA but rather may determine spatial configuration of the half-sites via protein-protein interaction. One possibility is that it may represent a dimerization interface. This assumption is consistent with recent reports that the receptor DNA binding domain by itself seems to contain a dimerization signal (Kumar, et al., 1988; Tsai, et al., 1988).

TABLE 1

Phenotypes of the Wild-Type and Mutant DNA Binding Domains

| element P | element D | GRE | ERE | TREp |
|---|---|---|---|---|
| GR | GR | + | – | – |
| $T_3R\beta$ | $T_3R\beta$ | – | + | + |
| GR | $T_3R\beta$ | (+) | – | – |
| $T_3R\beta$ | GR | – | + | – |
| ER | ER | – | + | – |
| GR | ER | + | – | |
| ER | GR | – | + | |

The phenotypes of GR-ER hybrids are from Green, et al., (1988). (+) indicates that a positive phenotype is dependent on the construct.

TABLE 2

Structure of Element P and Element D in GR and ER/TR Subfamilies

| Receptor | Element P | Element D |
|---|---|---|
| a) GR Subfamily | | |
| GR, MR, PR, AR | GSCKV | AGRND |
| | GSCKV | ASRND |
| b) ER Subfamily | | |
| ER | EGCKA | PATNQ |
| $T_3R\alpha$ | EGCKG | KYDSC |
| $T_3R\beta$ | EGCKG | KYEGK |
| RAR$\alpha$, RAR$\beta$ | EGCKG | HRDKN |
| $VD_3R$ | EGCKG | PFNGD |
| NGFI-B | EGCKG | LANKD |
| TR2 | EGCKG | RGSKD |
| v-erbA | EGCKS | TYDGC |
| ear2 | EGCKS | RSNRD |
| ear3 | EGCKS | RANRN |
| knirps | EGCKS | KNEGK |
| knirps-related | EGCKS | KNNGE |
| ERR1 | EACKA | PASNE |
| ERR2 | EACKA | PATNE |

DETAILED DESCRIPTION OF THE DRAWINGS

FIGS. 1A–1C. 1A) Comparison of amino acid sequences among the DNA binding domains of hGR, h$T_3R\beta$, and hER (for reference, see Evans, 1988). Upper numbers (1 to 9) correspond to the invariant nine cysteines found in the receptor DNA binding domains. Number adjacent to the sequences indicate amino-acid positions of each receptor. Colons show the identity of amino acids between hGR and h$T_3R\beta$ or h$T_3R\beta$ and hER. The h$T_3R\beta$ DNA binding domain contains two extra amino acids in the middle of the domain. 1B) Predicted zinc fingers based on those for rat GR18. Numbers 1 to 9 for cysteines are as in FIG. 1A. Conserved amino acids in hGR, h$T_3R\beta$, and hER are shown by one letter amino-acid code. Dots represent variable amino acids among these receptors. Two zinc ions (Zn) are chelated in a tetrahedral coordination by two clusters of four cysteines ($C_1$ to $C_4$ and $C_5$ to $C_8$), forming two "zinc fingers" (Finger 1 and Finger 2). The two fingers are separated by 15 (hGR and hER) or 17 (h$T_3R\beta$) amino acids consisting of Linker between the fingers. 1C) Structures of optimized hormone response elements for GR (GRE), ER (ERE), and $T_3R$ (TRE) (See Green and Chambon, 1988; Klock et al., 1987; and Glass et al., 1988). Each arrow indicates a "half site" of the HREs. These HREs consist of a palindromic pair of the half sites as shown by the arrows. Both GRE and ERE contain three gap nucleotides (nnn) between the half sites, but no such nucleotide is found in TREp (--). Dots in ERE and TREp indicate different nucleotides from those of GRE. Accordingly, ERE and TREp contain the same half site sequence.

FIG. 2. Transactivation of luciferase reporter plasmids by mutant receptors. The amino acid sequence of a parental hGRnx DNA binding domain is presented. The hGRnx contains the wild-type hGR DNA binding domain flanked by NotI and XhoI sites in the cDNA. Numbers 1 to 9 are as in FIG. 1A. The unmodified amino acid sequence of the h$T_3R\beta$ DNA binding domain is shown as GTG. GTG is a hybrid GR whose DNA binding domain has been replaced by that of h$T_3R\beta$. Substituted or inserted amino acids in mutant and GRsst are shown. Structures of chimeric GR DNA binding domains carrying local h$T_3R\beta$ (e.g. GTG7, GTG3A, and GTG6) or hRAR$\alpha$ (e.g. GRG8) sequences are also shown. Changed amino acids are presented. Mutants are designated according to the composition of their DNA binding domains; e.g. "GTG33" designates a mutant GR which has a DNA binding domain composed of both hGR and h$T_3R\beta$ sequences, and contains 33 different amino acids from the wild-type hGR sequence.

Each receptor expression plasmid was cotransfected into CV-1 cells with either glucocorticoid (MTV-LUC) or thyroid hormone ($\Delta$MTV-TREp-LUC) responsive reporter plasmids, and the cells were cultured in the absence or presence of 100 nM dexamethasone for 36 hours. Transactivation function of these receptors was judged by the induced luciferase activity from the reporter plasmids quantified as percentage of HGRNX and GTG activities upon MTV-LUC (MTV) (2,500 fold) and $\Delta$MTV- TREp-LUC (TREp) (200 fold), respectively. The activity below the background induction level (6 fold for MTV and two fold for TREp) is indicates as -. For the activity of GTG18 on TREp, the "(2)" indicates that the induction is not dependent on TREp.

Mutant cDNAs encoding DNA binding domains of GTG7, GTG3B, GRG8, GTG6, and GTG3A were obtained through an oligonucleotide-directed mutagenesis (Kunkel, et al., 1985) of the NotI-XhoI DNA fragment encoding the hGRnx DNA binding domain. Similarly, those for GTG32, GTG36B, GTG29, GTG33, and GTG36A were made by exchanging the NotI-XhoI fragment for the hT$_3$Rβ DNA binding domain. Mutants GRsst and GTsstG cDNAs contain a SstI linker (8-mer, New England Biolabs). Each of the NotI-XhoI cDNA fragments encoding mutant DNA binding domains was ligated with a large NotI-XhoI fragment obtained from pRShGRnx. To make GTG28, ClaI site was introduced into hT$_3$Rβnx DNA binding domain cDNA (corresponding to amino acids "ID" in the loop of the Finger 2. Because the hGRnx cDNA has the ClaI site at this position, the NotI-ClaI fragment of the hGRnx cDNA was replaced by that of hT$_3$Rβnx cDNA. All mutations were confirmed by the nucleotide sequencing. Construction of reporter plasmids MTV-LUC and ΔMTV-TREp-LUC was done using previously published methods. Receptor expression plasmid (1 μg), reporter plasmid (5 μg), β-galactosidase reference plasmid (5 μg), and carrier plasmid pGEM4 (9 μg) were cotransfected. Transfection of CV-1 cells (Umesono, et al., 1988) and an assay for the luciferase activity were done using published methods (de Wet, et al., 1987) except that the reference plasmid pRSV-βGAL was replaced by pRAS-βGAL which contains a human c-Ha-ras promoter (Ishii, et al., 1985) linked to the coding sequence of β-galactosidase in a pUC-derivative plasmid (pUCGALpA, kindly provided by Dr. Richard J.Rickles), and phenol red in the culture media was omitted after introduction of the plasmids into the cells.

FIG. 3. Identification of two distinct elements specifying the TREp+ and ERE+ phenotypes. Two parental DNA binding domains hGR and GTG, are presented by bold letters. In GTG identical amino acids to those in hGR are indicated by dots. Similarly, only different amino acids in mutant DNA binding domains from those of hGR are shown. The two regions (element P and D) are marked by boxes. Nomenclature of the mutants and numbers are the same as in FIG. 2. Mutant receptors were tested for transactivation function in the presence of one of the luciferase reporters carrying GREs (MTV-LUC), TREp (ΔMTV-TREp-LUC), or ERE (ΔMTV-ERE-LUC) after transient expression in CV-1 cells (±100 nM dexamethasone for 36 hours). Weak stimulation (2) by GTG15 on TREp is due to higher background activity by this mutant, and the 2% induction is not dependent on TREp. 100% induction of the luciferase activity by GTG on ΔMTV-ERE-LUC (ERE) is 10 fold, and— indicates no induction.

FIG. 3 Methods. An estrogen responsive reporter plasmid ΔMTV-ERE-LUC was constructed as follows: an oligonucleotide encoding a palindromic ERE (5'-TCAGGTCA-CAGTGACCTGA-3') (see Glass, et al., 1988) was inserted into the unique HindIII site of the ΔMTV-CAT plasmid, in which major GREs between position -190 and -88 of MTV-LTR were deleted; this generated ΔMTV-ERE-CAT; the CAT gene was subsequently replaced with the luciferase gene obtained from pSVOA/L-A Δ5' (de Wet, et al., 1987), giving ΔMTV-ERE-LUC. Mutant GTG21 is made from GTG32 by introducing the ClaI site as in GTG28 (FIG. 2). A small NotI-ClaI fragment of hGRnx was exchanged by that of GTG32-ClaI. GTG15 and GT8B were obtained through site-directed mutagenesis (Kunkel, et al., 1985) of the cDNAs encoding GTG21 and GTG3A DNA binding domains, respectively. Similarly GTG2 and GTG1 were made from hGRnx. Transfection and an assay of the luciferase activity were as in FIG. 2.

FIGS. 4A–4H. Induction of CAT activities by mutant receptors from the basal ΔMTV-CAT (ΔM), T3-responsive ΔMTV-TREp-CAT (TREp), and estrogen-responsive ΔMTV-ERE-CAT (ERE) reporters. Together with one of the reporters, indicated receptor expression plasmids from FIGS. 4A to 4H were transfected into CV-1 cells. The receptors were activated by adding 100 nM of dexamethasone (D) or 17β-estradiol (E2) for 36 hours. The "-" symbol indicates that the solvent ethanol was added. Structures of hGRnx, GTG, GTG8B, GTG3A, GTG2, and GTG1 were presented in FIGS. 2 and 3. The notation "no receptor" indicates that an expression plasmid encoding hT$_3$Rβ in the reverse orientation was cotransfected. hER; human estrogen receptor. 4E to 4H, changed amino acids are shown in a schematic figure for hGR zinc fingers. The calculated % conversions in the CAT assays are 4A ΔM (–) 0.4, (D) 0.5, TREp (–) 0.4, (D) 0.6, ERE (–) 0.6, (D) 1.0, 4B ΔM (–) 0.4, (D) 0.7, TREp (–) 0.3, (D) 0.8, ERE (–) 0.4, (D) 1.2, 4C ΔM (–) 1.8, (E$_2$) 1.6, TREp (–) 1.6, (E$_2$) 7.0, ERE (–) 1.8, (E$_2$) 78, 4D ΔM (–) 1.4, (D), 4.6, TREp (–) 1.1, (D) 74, ERE (–) 1.9, (D) 72, 4E ΔM (–) 0.5, (D) 1.3, TREp (–) 0.6, (D) 1.4, ERE (–) 1.2, (D) 20, 4F ΔM (–) 0.8, (D) 1.8, TREp (–) 0.9, (D) 3.5, ERE (–) 1.3, (D) 96, 4G ΔM (–) 0.5, (D) 0.7, TREp (–) 0.5, (D) 0.6, ERE (–) 1.0, (D) 88, 4H ΔM (–) 0.7, (D) 4.3, TREp (–) 0.7, (D) 87, ERE (–) 1.0, (D) 95.

FIGS. 4A–4H Methods. Reporter plasmids ΔMTV-CAT (Hollenberg, et al., 1988), ΔMTV-TREp-CAT (TREplM-CAT (Umesono, et al., 1988; Thompson and Evans, 1989), ΔMTV-ERE-CAT (see legend for FIG. 3), and an expression plasmid for hER37 were previously described. CV-1 cell transfection has been carried out as described in the legend for FIG. 2 except that the luciferase reporters were replaced by the CAT reporters. For the CAT assay (Gorman, et al., 1982), cell extracts corresponding to 30 units of β-galactosidase activity (Herbomel, et al., 1984) were incubated for 3 hours Calculation of % conversion for CAT activity was carried out as previously described (Thompson and Evans, 1989).

REFERENCES

The present specification refers to the following publications, each of which is expressly incorporated by reference herein.

1. Chang, C. and Kokontis, J., Biochem. Biophys. Res. Comm. 155, 971–977 (1988).
2. Chang, C., Kokontis, J., and Liao, S., Science 240, 324–326 (1988).
3. de Wet, J. R., Wood, K. V., Deluca, M., Helinski, Mol. Cell. Biol. 7, 725–737 (1987).
4. Evans, R. M., Science 240, 889–895 (1988).
5. Freedman, L. P., Luizi, B. F., Korszun, Z. R., Basavappa. R., Sigler, P. B., and Yamamoto, K. R., Nature 334, 543–546 (1988).
6. Giguere, V., Hollenberg, S. M., Rosenfeld, G. M., and Evans, R. M., Cell 46, 645–652 (1986).
7. Giguere, V., Ong, E. S., Segui, P., and Evans R. M., Nature 330, 624–629 (1987).
8. Giguere, V., Ong, E. S., Evans, R. M., and Tabin, C. J., Nature 337, 566–569 (1989).
9. Glass, C. K., Holloway, J. M., Devary, O. V., and Rosenfeld, M. G., Cell 54, 313–323 (1988).
10. Gorman, C. M., Moffat, L. F., and Howard, B. H., Mol. Cell. Biol. 2, 1044–1051 (1982).
11. Green S. and Chambon, P., Nature 325, 75–78 (1987).
12. Green S. and Chambon, P., Trends in Genetics 4, 309–314 (1988).
13. Green, S., Kumar, V., Theulaz, I., Wahli, W., and Chambon, P., EMBO J. 7, 3037–3044, (1988).

14. Ham, J., Thomson, A., Needham, M., Webb, P., and Parker, M., Nucl. Acids. Res. 16, 5263–5276 (1988).
15. Herbomel, P., Bourachot, B., and Yaniv, M., Cell 39, 653–662 (1984).
16. Hollenberg, S. M., Giguere, V., Segui, P. and Evans, R. M., Cell 49, 39–46 (1987).
17. Hollenberg, S. M. and Evans, R. M., Cell 55, 899–906 (1988).
18. Ishii, S., Merlino, G. T., and Pastan, I., Science 230, 1378–1381 (1985).
19. Klock, G., Strahle, U., and Schuetz, G., Nature 329, 734–736 (1987).
20. Kumar, V., Green, S., Stack, G., Berry, M., Jin, J.-R., and Chambon, P., Cell 51, 941–951 (1987).
21. Kumar, V. and Chambon, P., Cell 55, 145–156 (1988).
22. Kunkel, T. A., Proc. Natl. Acad. Sci., U.S.A. 82, 488–492 (1985).
23. Lubahn, D. B., Joseph, D. R., Sullivan, P. M., Willard, H. F., French, F. S., and Wilson, E. M., Science 240, 327–330 (1988).
24. Milbrandt, J., Neuron 1, 183–188 (1988).
25. Miller, J., McLachlan, A. D., and Klug, A., EMBO J. 4, 1609–1614 (1985).
26. Miyajima, N., Kadowaki, Y., Fukushige, S.-I., Shimizu, S., Semba, K., Yamanashi, Y., Matsubara, K., Toyoshima, K., and Yamamoto, T., Nucl. Acids Res. 16, 11057–11074 (1988).
27. Nauber, U., Pankratz, M. J., Kielin, A., Seifert, E., Klemm, U., and Jackle, H., Nature 336, 489–492 (1988).
28. Oro, A. E., Hollenberg, S. M., and Evans, R. M., Cell 55, 1109–1114 (1988a).
29. Oro, A. E., Ong, E. S., Margolis, J. S., Posakony, J. W., McKeown, M., and Evans, R. M., Nature 336, 493–496 (1988b).
30. Petkovich, M., Brand, N. J., Krust, A., and Chambon, P., Nature 330, 444–450, (1987).
31. Picard, D. and Yamamoto, K. R., EMBO J. 6, 3333–3340 (1987).
32. Rusconi, S. and Yamamoto, K. R., EMBO J. 6, 1309–1315 (1987).
33. Severne, Y., Wieland, S., Schaffner, W., and Rusconi, S., EMBO J. 7, 2503–2508, (1988).
34. Thompson, C. C. and Evans, R. M., Proc. Natl. Acad. Sci., U.S.A. 86, 3494–3498 (1989).
35. Tsai, S. Y., Carlstedt-Duke, J., Weigel, N. L., Dahlman, K., Gustafsson, J.-A., Tsai, M.-J., and O'Malley, B. W., Cell 55, 361–36 (1988).
36. Umesono, K., Giguere, V., Glass, C. K., Rosenfeld, M. G., and Evans, R. M., Nature 336, 262–265 (19–88).
37. Waterman, M. L., Adler, S., Nelson, C., Greene, G. L., Evans, R. M., and Rosenfeld, M. G., Mol. Endocrinol. 2, 14–21 (1988).
38. de Wet, J. R., Wood, K. V., Deluca, M., Helinski, D. R., and Subramani, S., Mol. Cell. Biol. 7, 725–737 (1987).

SPECIFICATION SUMMARY

From the foregoing description, one of ordinary skill in the art can understand that the present invention discloses steroid/thyroid hormone receptor DNA binding domain compositions that determine target gene specificity. The invention further discloses methods converting the target gene specificity of one receptor into the target gene specificity of another. Still further the invention discloses novel assays for identifying functional ligands for putative or "orphan" hormone receptors. These assays are especially useful since they avoid the necessity of constructing chimeric genes and proteins in order to search for ligands that can activate an orphan receptor.

Without departing from the spirit and scope of this invention, one of ordinary skill can make various changes and modifications to the invention to adapt it to various usages and conditions. As such, these changes and modifications are properly, equitable, and intended to be, within the full range of equivalence of the following claims.

What is claimed is:

1. Isolated steroid/thyroid hormone receptor DNA-binding domain compositions comprising element P peptide sequences of amino acid residues selected from the group consisting of GSCKV, EGCKA, EGCKG, EGCKS and EACKA, said sequences being functional to control target gene specificity in host cells normally deficient in such sequences.

2. Isolated steroid/thyroid hormone receptor DNA-binding domain compositions comprising element D peptide sequences of amino acid residues selected from the group consisting of AGRND, ASRND, PATNQ, KYDSC, KYEGK, HRDKN, PFNGD, LANKD, RGSKD, TYDGC, RSNRD, RANRA, KNEGK, KNNGE, PASNE and PATNE, said sequences being functional to control target gene specificity in host cells normally deficient in such sequences.

3. A mutant receptor selected from the group consisting of GTG8B, GTG3A, GTG2, and GTG1, wherein the DNA-binding domain of said receptor has the amino acid sequence shown in FIGS. 2 and 3.

4. A method for producing an isolated receptor protein that can activate both glucocorticoid receptor hormone response element (GRE) and estrogen receptor hormone response element (ERE), said method comprising:

(A) replacing the glycine residue between $C_3$ and $C_4$ of the glucocorticoid receptor with a glutamic acid residue, or (B) replacing the glutamic acid residue between $C_3$ and $C_4$ of the estrogen receptor with a glycine residue, and thereby (C) producing said isolated receptor protein.

5. Isolated receptor protein that can activate both glucocorticoid receptor hormone response element (GRE) and estrogen receptor hormone response element (ERE) produced according to claim 4.

6. A method for identifying a ligand(s) that activates an orphan receptor, said method comprising:

(A) introducing a mutated orphan receptor into receptor-deficient cells, wherein said cells contain a reporter gene functionally linked to a preselected hormone response element, and wherein nucleic acids encoding at least three amino acid residues of the P element of said receptor have been mutated so that said receptor activates said preselected hormone response element;

(B) challenging said cells with candidate ligand(s) which can potentially bind with the ligand-binding domain of said mutated orphan receptor;

(C) monitoring induction of the reporter gene (s); and (D) thereby identifying ligand(s) that activate said orphan receptor.

7. A method for identifying ligand(s) that activate an orphan receptor, said method comprising:

contacting endogenous-receptor-deficient host cells with candidate ligand(s) wherein said host cells contain a reporter gene functionally linked to a preselected hormone response element, and an exogenous gene encoding a mutated orphan exogenous gene, said receptor protein produced by mutating nucleic acids encoding at least three amino acid residues of the P element of the orphan receptor so that said resulting mutated receptor activates said preselected hormone response element, wherein said hormone response element, upon activation, induces expression of said reporter gene(s);

monitoring induction of said reporter gene(s); and identifying ligand(s) that activate said orphan receptor.

8. A method according to any one of claims 6 or 7 wherein said P element region is mutated by site-directed mutagenesis.

9. A method of any one of claims 6–7 wherein said cell is a CV-1 cell.

10. A method according to any one of claims 6–7 wherein said reporter gene is selected from the group consisting of a chloramphenicol acetyltransferase gene and a firefly luciferase gene.

* * * * *